(12) United States Patent
Oberholzer

(10) Patent No.: US 7,402,296 B2
(45) Date of Patent: Jul. 22, 2008

(54) METHOD FOR STABILIZING COPPER HYDROXIDE

(75) Inventor: Matthew Richard Oberholzer, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/661,516

(22) PCT Filed: Aug. 30, 2005

(86) PCT No.: PCT/US2005/030986

§ 371 (c)(1), (2), (4) Date: Feb. 26, 2007

(87) PCT Pub. No.: WO2006/028853

PCT Pub. Date: Mar. 16, 2006

(65) Prior Publication Data

US 2007/0270601 A1    Nov. 22, 2007

(51) Int. Cl.
*C01G 3/02* (2006.01)
*A01N 25/00* (2006.01)
*C07F 1/08* (2006.01)

(52) U.S. Cl. ............... 423/604; 424/404; 424/405; 424/633; 556/113

(58) Field of Classification Search ........... 423/604; 556/113; 424/404, 405, 633
See application file for complete search history.

(56) References Cited

U.S. PATENT DOCUMENTS

| 1,800,828 | A | 4/1931 | Furness |
| 1,867,357 | A | 7/1932 | Furness |
| 2,525,242 | A | 10/1950 | Rowe |
| 2,536,096 | A | 1/1951 | Rowe |
| 2,666,688 | A * | 1/1954 | Furness ............... 423/604 |
| RE24,324 | E | 5/1957 | Furness et al. |
| 2,924,505 | A | 2/1960 | Page, Jr. et al. |
| 3,428,731 | A | 2/1969 | Furness et al. |
| 3,628,920 | A | 12/1971 | Barker |
| 3,635,668 | A | 1/1972 | Barker |
| 4,404,169 | A | 9/1983 | Ploss et al. |
| 4,418,056 | A * | 11/1983 | Gonzalez ............... 424/631 |
| 4,447,336 | A * | 5/1984 | Vandersall ............... 252/7 |
| 4,490,337 | A | 12/1984 | Richardson |
| 4,567,220 | A * | 1/1986 | Schuler et al. ............ 524/413 |
| 4,614,640 | A * | 9/1986 | Ploss et al. ............... 423/35 |
| 4,808,406 | A | 2/1989 | Brinkman |
| 4,944,935 | A | 7/1990 | Langner et al. |
| 5,462,738 | A | 10/1995 | LeFiles et al. |
| 2002/0136685 | A1 | 9/2002 | Huato et al. |

FOREIGN PATENT DOCUMENTS

| DE | 195 43 803 A1 | 5/1997 |
| EP | 0 080 226 B1 | 11/1982 |
| WO | WO 02/083566 A2 | 10/2002 |

OTHER PUBLICATIONS

Harry B. Weiser et al., "Hydrous Cupric Hydroxide and Basic Cupric Sulfates", J. Phys. Chem., vol. 64, pp. 503-505 (1942).
J. Komorowska-Kulik, "Zeszyty Naukowe Politechnii Sltaskiej", Series: Chemistry 2001, 142, pp. 59-66.

* cited by examiner

*Primary Examiner*—P. Nazario-Gonzalez

(57) ABSTRACT

Disclosed is a method of stabilizing copper(II) hydroxide, the method comprising the sequential steps of: (a) combining copper(II) hydroxide, a water-soluble phosphate and water to form a mixture; and (b) drying the mixture. Also disclosed is stabilized copper(II) hydroxide prepared according to said method and a composition comprising stabilized copper(II) hydroxide prepared according to said method and at least one of a surfactant, a solid diluent or a liquid diluent.

10 Claims, No Drawings

METHOD FOR STABILIZING COPPER HYDROXIDE

BACKGROUND OF THE INVENTION

Copper(II) hydroxide, also known as cupric hydroxide and having the chemical formula $Cu(OH)_2$, has a wide variety of commercially important uses, including as a mordant and pigment in dyeing textile and paper fibers, in the preparation of catalysts and other copper compounds, in marine paints, and in fungicides and bactericides.

Even under ambient conditions copper(II) hydroxide is thermodynamically unstable relative to decomposition to copper(II) oxide. This inherent instability complicates the manufacture, distribution and storage of copper(II) hydroxide and compositions containing it. The change of chemical composition of copper(II) hydroxide to copper(II) oxide can be gradual or rapid and is typically accompanied by change of the blue color characteristic of copper(II) hydroxide to a more greenish hue and ultimately the black color of copper(II) oxide.

Although copper(II) hydroxide is thermodynamically unstable, whether or not significant decomposition occurs as well as the rate of decomposition (i.e. the kinetics of decomposition) is affected by a variety of conditions. Increasing temperature is well known to promote the decomposition of copper(II) hydroxide to copper(II) oxide. H. B. Weiser et al. *J. Am. Chem. Soc.* 1942, 64, 503-508 report that under otherwise constant conditions, the rate of transformation of copper (II) hydroxide to copper(II) oxide is higher the smaller the crystals of the copper(II) hydroxide. H. B. Weiser et al. also report that copper(II) hydroxide gels prepared by addition of a slight excess of alkali to a cupric salt solution decompose even at room temperature and even a trace of alkali accelerates the decomposition.

The patent literature discloses a variety of processes for the commercial manufacture of copper(II) hydroxide. U.S. Pat. Nos. 2,924,505, 3,428,731, 3,628,920 and Re 24,324 disclose processes involving phosphate. U.S. Pat. Nos. 4,490,337 and 4,808,406 disclose processes involving carbonate; the latter process provides a product comprising considerable copper carbonate in addition to copper hydroxide. U.S. Pat. Nos. 1,800,828, 1,867,357, 2,525,242, 2,536,096 and 3,635,668 discloses processes involving ammonia. The processes of U.S. Pat. Nos. 2,525,242 and 2,536,096 involve oxidation of copper metal in the presence of ammonia, and U.S. Pat. No. 4,944,935 discloses a similar process substituting ammonium ion for all or part of the ammonia. The other processes start with a soluble copper salt, typically copper(II) sulfate. U.S. Pat. No. 4,404,169, European Patent EP 80226 B1 and PCT Patent Publication WO 02/083566 A2 describe processes starting with copper(II) oxychloride. J. Komorowska-Kulik, *Zeszyty Naukowe Politechniki Sltaskiej, Series: Chemistry* 2001, 142, 59-66 discloses a process wherein an aqueous suspension of copper(II) oxychloride is contacted with aqueous sodium hydroxide in the presence of glycerol as stabilizer. None of these processes pertain to stabilizing copper(II) hydroxide prepared by another process.

The processes commercially used to prepare copper(II) hydroxide provide products in forms different from the gels described by Weiser et al. and have greater kinetic stability. However, reaction temperatures for these processes are limited to not much above room temperature, and the storage life of the copper(II) hydroxide products of these processes may be limited, particularly at temperatures significantly above room temperature. U.S. Pat. No. 3,428,731 states that crystalline copper hydroxide prepared by the phosphate-based process of U.S. Pat. No. Re 24,324 is stable for indefinite periods at temperatures not exceeding 120° F. (48.9° C.). U.S. Pat. No. 2,536,096 indicates for an ammonia-based oxidation process that at temperatures above about 87° F. (31° C.) cupric oxide is also formed, and this becomes the product at temperatures above 140° F. (60° C.). U.S. Pat. No. 4,490,337 states that the reaction slurry in the carbonate-based process may decompose at temperatures above 32° C., but discloses examples drying the product at higher temperatures; a product dried at 60° C. was found to be highly amorphous by x-ray analysis.

For the phosphate-based process disclosed in U.S. Pat. Nos. Re 24,324 and 3,428,731 a reaction sequence is suggested where sodium phosphate is used to form copper(II) sodium phosphate as an intermediate, which is then treated with sodium hydroxide to form copper(II) hydroxide and regenerate sodium phosphate. U.S. Pat. No. 3,428,731 states that from the reaction mixture a dry, solid product is obtained by separating the solids from the mother liquor, washing, drying and grinding. U.S. Pat. No. 3,428,731 also states that a minor amount of phosphate can be included in the product as calcium phosphate by substituting calcium hydroxide for at least part of the sodium hydroxide.

U.S. Pat. No. 2,924,505 describes a process for preparing copper hydroxide containing a bound phosphorus content (expressed as $PO_4$) of substantially not less than 3.5%. Any substantial deviation below the minimum average content of bound phosphorus is said to lead to the formation of cupric oxide. A non-crystalline product is claimed. The product is prepared by adding streams of aqueous copper sulfate and sodium hydroxide solutions to a slurry formed from sodium phosphate and copper sulfate. The precipitated product is washed to remove water-soluble impurities, including unbound phosphate, and then dried at a temperature around 140° F. (60° C.).

U.S. Pat. No. 3,628,920 describes a process for preparing a copper hydroxide-phosphorus complex having a bound phosphorus content of at least about 2% by weight calculated as $P_2O_5$. The complex is prepared by mixing copper sulfate and phosphoric acid with sodium hydroxide such that the pH is maintained between about 10 to 11.5. As the complex formed is stated to decompose to copper oxide when held at temperatures of 112° F. (44° C.) for even 0.5 to 10 minutes, a reaction temperature range of 85-110° F. (29-43° C.) is specified, and temperatures below 85° F. (29° C.) are recommended for longer reaction times. The product is washed thoroughly and then dried at temperatures up to about 180° F. (82° C.). The product in form of a wet cake is stated to be stable at temperatures up to 150° F. (66° C.) over relatively long periods of time.

U.S. Pat. No. 4,404,169 describes a process for preparing copper(II) hydroxide involving contacting copper oxychloride with an alkali metal or alkaline earth metal hydroxide in the presence of phosphate ions as stabilizer. The temperature is stated to desirably not exceed 35° C., preferably 20 to 25° C., to avoid transformation of some of the copper hydroxide to the oxide. The precipitated copper hydroxide is recovered, washed, and again suspended in an aqueous phase and treated with an acid phosphate to bring the pH to a value of 7.5 to 9. The copper hydroxide is then separated from the aqueous mixture, washed, and suspended in water or dried. European Patent 80226 B1 describes the aqueous mixture being used as a fungicide. Neither reference provides stability data.

PCT Patent Publication WO 02/083566 A2 describes a process for preparing copper hydroxide containing copper phosphate. In this process an aqueous solution of cupric oxychloride is combined with aqueous sodium hydroxide in a continuous reactor comprising a high-shear agitation system. The reaction mass is held at 20-24° C. to complete the reaction, and then treated with an aqueous solution of orthophosphoric acid. In a strongly agitated reactor, the reaction mixture is then brought to pH 8-8.2 by adding an aqueous solution of cupric chloride, resulting in precipitation of copper phosphate. The reaction mass is collected using vacuum filtration, washed with softened water, and dried using a spray drier. No information regarding stability is disclosed.

German Patent Publication DE 19543803A1 describes a process for preparing copper(II) hydroxide phosphate from copper(II) hydroxide and a stoichiometric amount of phosphoric acid for use as an artist's pigment. The product is collected by filtration; the filter cake is washed and then dried.

Minimizing decomposition of copper(II) hydroxide during its storage and use is important for many of its applications including as a fungicide and bactericide. To evaluate the stability of plant protection products, the Food and Agriculture Organization of the United Nations has described an accelerated storage procedure, Method MT 46, involving heating at 54±2° C. for 14 days (see *Manual on Development and Use of FAO Specifications for Plant Protection Products*, Fifth Edition, January 1999, sections 3.6.2 and 5.1.5). The elevated temperature in the procedure serves to assess stability if the products are stored or used at elevated temperatures, and also to simulate the aging process at ambient conditions but in a shorter period of time. The decomposition of copper (II) hydroxide to copper(II) oxide can be evaluated by a number of methods, including x-ray diffraction and colorimetric measurement.

Although effective methods are available to prepare copper (II) hydroxide products and to assess their kinetic stability, copper(II) hydroxide products having better storage stability and greater resistance to heat are still needed. Particularly desirable are methods for stabilizing (i.e. increasing the kinetic stability) of copper(II) hydroxide products prepared by known processes.

SUMMARY OF THE INVENTION

This invention is directed to a method of stabilizing copper (II) hydroxide, the method comprising the sequential steps of:

(a) combining copper(II) hydroxide, a water-soluble phosphate and water to form a mixture; and (b) drying the mixture.

This invention also relates to stabilized copper(II) hydroxide prepared according to said method, and to a composition comprising stabilized copper(II) hydroxide prepared according to said method and at least one of a surfactant, a solid diluent or a liquid diluent.

DETAILED DESCRIPTION OF THE INVENTION

As referred to herein, a water-soluble phosphate includes water-soluble chemical compounds containing orthophosphate or polyphosphate including oligomers such as pyrophosphate, trimetaphosphate or hexametaphosphate. Water-soluble means solubility in water at 20° C. of at least 1 g per liter. Examples of water-soluble phosphates are phosphoric acid, sodium dihydrogenphosphate, sodium hydrogenphosphate, sodium phosphate, potassium dihydrogenphosphate, potassium hydrogenphosphate and ammonium dihydrogenphosphate, which may be anhydrous or hydrated.

Embodiments of the present invention include:

Embodiment 1

The method wherein the water-soluble phosphate is in amount of at least about 0.1 mol % relative to the copper(II) hydroxide.

Embodiment 2

The method of Embodiment 1 wherein the water-soluble phosphate is in amount of at least about 0.3 mol % relative to the copper(II) hydroxide.

Embodiment 3

The method of Embodiment 2 wherein the water-soluble phosphate is in amount of about 0.3 mol % to 2 mol % relative to the copper(II) hydroxide.

Embodiment 4

The method wherein the water-soluble phosphate is in amount of not more than about 10 mol % relative to the copper(II) hydroxide.

Embodiment 5

The method of Embodiment 4 wherein the water-soluble phosphate is in amount of not more than about 5 mol % relative to the copper(II) hydroxide.

Embodiment 6

The method of Embodiment 5 wherein the water-soluble phosphate is in amount of not more than about 2 mol % relative to the copper(II) hydroxide.

Embodiment 7

The method wherein the water-soluble phosphate is a phosphate of an alkali metal or ammonium.

Embodiment 8

The method of Embodiment 7 wherein the water-soluble phosphate is a phosphate of sodium or potassium.

Embodiment 9

The method of Embodiment 8 wherein the water-soluble phosphate is sodium hydrogenphosphate.

Embodiment 10

The method of Embodiment 8 wherein the water-soluble phosphate is potassium hydrogenphosphate.

Embodiment 11

The method of Embodiment 8 wherein the water-soluble phosphate is sodium dihydrogen phosphate.

Embodiment 12

The method wherein in (a) a dry copper(II) hydroxide powder is added to a combination of water and the water-soluble phosphate.

Embodiment 13

The method wherein in (a) a slurry of copper(II) hydroxide in water is added to a combination of water and the water-soluble phosphate.

Embodiment 14

The method wherein in (a) copper(II) hydroxide is added as a high moisture solid to a combination of water and the water-soluble phosphate.

Embodiment 15

The method wherein in (a) the water-soluble phosphate is added to a mixture of the copper(II) hydroxide and water.

Embodiment 16

The method wherein in (b) the mixture is dried by spray drying.

Embodiment 17

The method wherein the copper(II) hydroxide is crystalline.

Embodiment 18

The method wherein the copper(II) hydroxide is prepared by a process using ammonia.

Embodiment 19

The method of Embodiment 18 wherein the copper(II) hydroxide is prepared by oxidizing copper metal with oxygen in the presence of ammonia.

Embodiment 20

The method wherein the copper(II) hydroxide is prepared by a process using phosphate.

Embodiment 21

The method wherein the copper(II) hydroxide is prepared by a process using carbonate.

Embodiment 22

The method further comprising recovering the dried mixture.

Embodiment 23

The method of Embodiment 22 further comprising mixing the recovered dried mixture with at least one of a surfactant, a solid diluent or a liquid diluent to form a stabilized copper (II) hydroxide composition.

Embodiment 24

The method of Embodiment 22 further comprising mixing the recovered dried mixture with at least one other biologically active compound or agent to form a multi-component pesticide.

In the method of the present invention the copper(II) hydroxide, water-soluble phosphate and water are combined, typically in a suitably sized container or reactor, preferably fitted with a mechanical means for stirring or other agitation. The materials can be combined in any order, but mixing may be facilitated by adding the copper hydroxide to a combination of water and the water-soluble phosphate. The water-soluble phosphate need not be fully dissolved in the water before adding the copper hydroxide, but is preferred because prior complete dissolution ensures that all of the water-soluble phosphate treats the copper(II) hydroxide and no solid water-soluble phosphate starting material remains. Agitation of the reactor contents during the addition is helpful to ensure good contact between the copper(II) hydroxide crystals and the aqueous solution of water-soluble phosphate. The materials can be combined and mixed at temperatures between the melting point of water (e.g., about 0° C.) and about 50° C., but the method works well near room temperature, i.e. about 20 to 25° C., which is most convenient.

The minimum amount of water needed for forming the mixture is the quantity needed to dissolve the water-soluble phosphate at the chosen process temperature. There is no particular upper limit on the amount of water, but most satisfactory is an amount of water that does not reduce the viscosity of the copper hydroxide slurry and increase its volume to the extent that operation of the mixing means is not safe or efficient or that further processing (e.g., transfer of the slurry out of the reaction, use of milling equipment, use of drying equipment) is complicated or rendered less efficient. As an amount of water substantially in excess of the amount needed to dissolve the water-soluble phosphate typically provides little advantage, the amount of water added is preferably little more than the amount needed to dissolve the water-soluble phosphate.

To the water is added the water-soluble phosphate in the amount of at least 0.1 mol %, preferably about 0.3 to 2 mol %, and most preferably about 0.7 mol % phosphate ion relative to the copper(II) hydroxide charge. Although larger amounts of water-soluble phosphate (e.g., up to about 10 mol %) can be used, smaller amounts (e.g., up to 2 mol %) are typically sufficient and therefore preferable. Suitable water-soluble phosphates, as referred to herein, include water-soluble chemical compounds containing orthophosphate or polyphosphate including oligomers such as pyrophosphate, trimetaphosphate or hexametaphosphate. Water-soluble means solubility in water at 20° C. of at least 1 g per liter. Examples of water-soluble phosphates are phosphoric acid, sodium dihydrogenphosphate, sodium hydrogenphosphate, sodium phosphate, potassium dihydrogenphosphate, potassium hydrogenphosphate and ammonium dihydrogenphosphate, which may be anhydrous or hydrated. Typically the water-soluble phosphate in the present method is a phosphate of an alkali metal or ammonium; preferably the water-soluble phosphate is a phosphate of sodium or potassium. Also typically the water-soluble phosphate comprises a form of orthophosphate, preferably dihydrogenphosphate or hydrogenphosphate, most preferably hydrogenphosphate. Preferred is sodium hydrogenphosphate ($Na_2HPO_4$), sodium dihydrogenphosphate ($NaH_2PO_4$), potassium hydrogenphosphate ($K_2HPO_4$) or potassium dihydrogenphosphate ($KH_2PO_4$); more preferred is sodium hydrogenphosphate or potassium hydrogenphosphate; most preferred is sodium hydrogenphosphate.

The copper(II) hydroxide is added either as a dry powder (e.g., <5% moisture), as a slurry in water, or preferably as a high moisture solid (e.g., wet cake, as is typically obtained by filtration of the copper hydroxide reaction mixture). The copper hydroxide may prepared by any process that gives copper hydroxide stable enough to isolate as starting material for the present method. These processes include, for example, processes involving formation of copper(II) hydroxide in the presence of ammonia (i.e. an ammonia process) such as oxidation of copper metal with oxygen (e.g., air), processes involving treating copper salts with phosphate followed by base (i.e. a phosphate process) and processes involving treating copper salts such as copper oxychloride or oxysulfate with hydroxide. The copper(II) hydroxide must be blue in color as indication it has not already begun to significantly decompose. Preferably the copper(II) hydroxide is crystalline material rather than a gel or amorphous solid. Of note for the method of the present invention is copper(II) hydroxide prepared by an ammonia process, particularly a process involving oxidation of copper metal with oxygen in the presence of ammonia. The method of the present invention can also significantly improve the stability of copper(II) hydroxide prepared by other processes, including most notably processes involving phosphate.

Mixing may be achieved by mechanical means. No special equipment is required, but it is preferable to use a dispersion blade impeller mounted on an overhead mixer. The minimum time for mixing the reactor contents depends upon the reactor size and the quantities of materials charged. Extended mixing times do not affect the stabilization method adversely.

Following the treatment step, the stabilized solid copper (II) hydroxide is obtained by the evaporation of water from the slurry. Drying is preferably accomplished using a spray dryer (i.e. spray drying), but an agitated pan dryer, thin-film dryer, drum dryer, tray dryer or combinations thereof can be used. Drying conditions will depend upon the desired moisture level in the copper hydroxide powder. Filtration, as a means to separate the water from the copper hydroxide is found to adversely affect the stabilization of the copper(II) hydroxide; an essential aspect of the present invention is that the aqueous water-soluble phosphate solution is evaporated onto the copper hydroxide particles. Therefore according the present method the slurry comprising copper(II) hydroxide and a water-soluble phosphate is dried without filtration (or separation of solids by other means such as centrifugation) before drying. Accordingly, filtration of the slurry and washing (i.e. rinsing) the filter cake with water before drying would be contrary to the present method.

After the stabilized solid copper(II) hydroxide is dried, it is typically recovered (i.e. collected) from the dryer for use in commercially important applications such as preparation of fungicidal and bactericidal compositions. The dried stabilized solid copper(II) hydroxide generally has a physical character similar to that of the dried starting copper(II) hydroxide, which typically is a powder. The dried stabilized solid copper(II) hydroxide powder can be either agglomerated to form a friable cake or loose depending upon such factors as the nature of the dryer. Spray dryers generally dry the stabilized solid copper(II) hydroxide in the form of a loose powder. Methods for recovering dried solids from dryers are well known in the art, and optimal methods will be obvious to one skilled in the art depending on the configuration of the dryer and physical nature of the dried product. Spray dryers often comprise a cone-shaped cavity which serves to collect the dried powder and direct it to an narrow bottom opening; the powder can then be easily directed to a storage container, a mixer, a mill, or other processing equipment. For preparation of fungicidal and bactericidal compositions the recovered dried copper(II) hydroxide is typically mixed with at least one of a surfactant, a solid diluent or a liquid diluent. For example, mixing with water as liquid diluent forms an aqueous suspension composition. Multi-component pesticides can be formed by mixing the recovered dried stabilized solid copper(II) hydroxide with at least one other biologically active compound or agent.

Once the copper(II) hydroxide has been treated, its particle size can be reduced using various milling devices, with no adverse effect on the stabilization. If particle size is to be reduced, the copper(II) hydroxide is preferably milled while still in the slurry, that is, prior to the evaporation of water (e.g., by spray drying). However, milling of the dried copper(II) hydroxide does not adversely affect its stability.

The present stabilization method can be practiced in discreet batches or in continuous or semi-continuous operation.

The present method provides the significant advantage in that copper(II) hydroxide can be stabilized such that it does not chemically transform to copper oxide nor does its blue color degrade substantially when subjected to elevated temperatures. Such behavior is observed when the copper hydroxide is heated either alone, as a powder, or as a mixture with water. Another advantage to the method is that the stabilization of copper hydroxide can be achieved after the copper hydroxide has been made. This is particularly useful because the stabilization method can be applied to copper hydroxide produced by any of the commercial processes and does not require modification of their process conditions. Furthermore while the present method stabilizes the copper (II) hydroxide the method does not greatly modify the assay of the copper(II) hydroxide in regards to, for example, percent copper, or in regards to particle size.

Without further elaboration, it is believed that one skilled in the art using the preceding description can utilize the present invention to its fullest extent. The following Examples are, therefore, to be construed as merely illustrative, and not limiting of the disclosure in any way whatsoever.

ANALYTICAL EXAMPLES

The stability of copper(II) hydroxide is desirably measured at elevated temperatures both to assess stability if the copper (II) hydroxide is stored or used at elevated temperatures and to simulate over a shortened time aging at lower temperatures. Several testing procedures to assess the stability of powdered copper(II) hydroxide are now described. In these procedures decomposition of copper(II) hydroxide is conveniently measured colorimetrically, as copper(II) hydroxide has a bright blue color lost during its decomposition; copper(II) oxide is black. The "Oven Test Method" in Analytical Example 1 involves heating dry copper(II) hydroxide powder at 54° C., as does FAO Method MT 46 cited in the Background of the Invention. As copper(II) hydroxide may also be stored and used as an aqueous slurry or suspension, the "Hot Water Test Method" in Analytical Example 2 and the "Hot Water Ramp Test Method" involve heating an aqueous slurry of copper(II) hydroxide.

Analytical Example 1

Oven Test Method

In this test, identified herein as the "oven test" method, a quantity of copper(II) hydroxide powder is placed in a glass container and sealed with a lid. The color of the powder in the glass container is measured using a calorimeter (for example, Colorport by Color Instruments, Inc., Ft. Lauderdale, Fla., item #34707X) and the "b" value according to the CIELAB color model (whose development was sponsored by the International Commission on Illumination) is recorded. According to the CIELAB color model, the "b" values of blue materials are negative numbers; the greater the blue intensity, the larger the negative number. The sealed glass container is placed in an oven maintained at a constant temperature of 54° C. The container is removed periodically for additional measurements, taking care to mix the contents of the container prior to measuring the color.

Analytical Example 2

Hot Water Test Method

In this test, identified herein as the "hot water test", a quantity of copper hydroxide(II) powder is mixed with water in a suitably sized glass container. A typical ratio is 5 g of $Cu(OH)_2$ to 100 g of water. The slurry is heated over 5 to 15 minutes with mixing to at least 70° C. and held at this temperature while being mixed for at least 30 minutes. Alternatively, higher temperatures up to 90° C. can be used. The color of the slurry is observed throughout the exposure to elevated temperature. After the desired exposure time has elapsed, the slurry is cooled and transferred into a glass container and sealed with a lid. The color of the slurry is then measured with a calorimeter such as the one described for Analytical Example 1.

Analytical Example 3

Hot Water Ramp Test Method

In this test, identified herein as the "hot water ramp test", involves subjecting the slurry formed as described for Analytical Example 2 to increasing temperatures, that is, 30 minutes at 70° C. followed immediately by 30 minutes at 80° C. followed immediately by 30 minutes at 90° C. In this variation, mixing is accomplished through vortex generation, and a condenser is used to minimize the evaporative loss of water. Measurement of the color is accomplished as described for Analytical Examples 1 and 2.

EXAMPLES OF THE PRESENT METHOD

Example 1

Method Treating Cupric Hydroxide Prepared from Ammonia Process with Sodium Hydrogenphosphate and Spray Drier A plastic container was charged with sodium hydrogenphosphate ($Na_2HPO_4$, 3.5 g, 24.7 mmol) followed by water (415 g). The contents of the plastic container were mixed until a clear solution was obtained. Then into the plastic container was charged commercially available copper hydroxide powder (commercially available technical grade comprising copper(II) hydroxide crystals prepared by a process oxidizing copper metal in the presence of ammonia, 350 g, 3.59 mol). (Therefore the amount of phosphate was 0.69 mol % relative to the copper hydroxide, equivalent also to about 0.67% by weight as $PO_4$ and 0.50% by weight as $P_2O_5$.) The contents of the container were mixed for 15 minutes at 500 RPM using a dispersion blade (for example, a "design E" dispersion blade, by Indco, Inc., New Albany, Ind.). The resulting slurry was screened through a 50-mesh wire screen to remove a minimal amount of agglomerates. The screened slurry was fed to a spray drier (GEA Niro, Copenhagen) at 30 mL/minute. The approximate dimensions of the spray dryer were 3 feet (0.91 m) in diameter by 6 feet (1.83 m) tall. The outlet temperature of the spray dryer ranged between 70 and 95° C. during the spray drying process. A blue powder was produced with a moisture level of 1.0% measured by a moisture balance and having an average "b" value of −8.07 calculated as the mean of 3 measurements.

Both the treated copper hydroxide powder and the untreated copper hydroxide technical powder were subjected to the hot water test as described in Analytical Example 2. After 5 minutes at 70° C., the slurry consisting of untreated copper hydroxide technical and water had already turned a dark green color (i.e., "b">0). After 30 minutes between 67.9° C. and 71.4° C., the slurry consisting of the treated copper hydroxide and water remained blue. After cooling, the "b" value of the slurry was −5.53.

Both the treated copper hydroxide powder and the untreated copper hydroxide technical powder were subjected to the oven test as described in Analytical Example 1. Average "b" values were calculated as the means of 3 measurements. Table 1 lists the average "b" values for the two copper hydroxide powders as a function of time in the oven.

TABLE 1

Effect of Oven Heating on Untreated and Treated Copper Hydroxide

| Untreated copper hydroxide | | Treated copper hydroxide | |
| --- | --- | --- | --- |
| Time (days) | "b" value | Time (days) | "b" value |
| 0 | −8.15 | 0 | −8.07 |
| 7 | −5.61 | 6 | −7.81 |
| 12 | −4.02 | 11 | −7.60 |
| 18 | 9.92 | 17 | −7.56 |
| 27 | 9.25 | 26 | −7.36 |

As can be seen from Table 1, the copper(II) hydroxide treated by the present stabilization method has only a small decrease in blue color while being heated in the oven at 54° C. over 26 days. In contrast, the untreated copper(II) hydroxide rapidly degrades at 54° C.

Example 2

Method Treating Cupric Hydroxide with Sodium Hydrogenphosphate and Vacuum Oven

A 1000-mL glass round bottom flask was charged with sodium hydrogenphosphate ($Na_2HPO_4$, 2.0 g, 14.1 mmol), followed by water (200 g). The contents of the flask were stirred with a magnetic stir bar until a clear solution was obtained. Then the flask was charged with 156 g of copper(II) hydroxide wet cake (approximately 36% water by weight; obtained from a manufacturing plant using a process oxidizing copper metal in the presence of ammonia). (Therefore the amount of phosphate was 1.38 mol % relative to the copper hydroxide, equivalent also to about 1.3% by weight as $PO_4$ and 2.0% by weight as $P_2O_5$.) The contents were again stirred with a magnetic stir bar until a smooth slurry was obtained. Then the flask was sealed and stored at ambient temperature for two days. The blue slurry was then poured into a drying tray constructed of glass. A small amount of water was used to assist the transfer. The tray was placed in a vacuum oven heated to between 45 and 50° C. and maintained at a reduced pressure between 2.4 psia and 4.9 psia (between 16.7 and 33.6 kPa). A slight flow of nitrogen gas was passed through the oven throughout the duration of drying process to assist with the removal of water. After approximately 24 h, the tray was removed from the oven, and the product was removed as a dry, light blue cake of powder having a "b" value of −11.32. X-ray powder diffraction analysis of the treated powder was consistent with copper hydroxide.

The dried copper hydroxide powder was subjected to the hot water test as described in Analytical Example 2. After 30 minutes at or above 70° C., the slurry consisting of the treated copper hydroxide and water remained blue. After cooling, the "b" value of the slurry was −4.89.

Example 3

Method Treating Cupric Hydroxide Prepared from Phosphate Process with Sodium Hydrogenphosphate and Spray Drier A plastic container was charged with sodium hydrogenphosphate ($Na_2TPO_4$, 3.0 g, 21.1 mmol) followed by water (400 g). The contents of the plastic container were mixed until a clear solution was obtained. Then into the plastic container was charged commercially available copper hydroxide powder (commercially available technical grade comprising copper(II) hydroxide crystals prepared by the phosphate process, 150 g, 3.59 mol, 50 g each from three separate lots). (Therefore the amount of phosphate was 1.37 mol % relative to the copper hydroxide, equivalent also to about 1.32% by weight as $PO_4$ and 1.96% by weight as $P_2O_5$.) The contents of the container were mixed for 15 minutes at 500 RPM using a dispersion blade (for example, a "design E" dispersion blade, by Indco, Inc., New Albany, Ind.). The resulting slurry was screened through a 50-mesh wire screen to remove a minimal amount of agglomerates. The screened slurry was fed to a spray drier (GEA Niro, Copenhagen) at 30 mL/minute as described in Example 1. A blue powder was produced having an average "b" value of −10.59 as the mean of three measurements.

Both the treated copper hydroxide powder and the untreated copper hydroxide technical powder were subjected to the hot water test as described in Analytical Example 2. After 15 minutes at 70° C., the slurry consisting of untreated copper hydroxide technical and water had already turned a dark green color (i.e., "b">0). After 30 minutes at 70° C. or greater, the slurry consisting of the treated copper hydroxide and water remained blue. After cooling, the average "b" value of the slurry was −9.11 as the mean of three measurements.

Formulation/Utility

The stabilized copper(II) hydroxide prepared according to the present method can be used in all the ways that copper(II) hydroxide may be used. Because of its stabilization, the copper(II) hydroxide prepared by the present method is particularly useful as an active ingredient in fungicides and bactericides. In fungicide and bactericide products, copper(II) hydroxide is generally used as a formulation or composition with an agriculturally suitable carrier comprising at least one of a liquid diluent, a solid diluent or a surfactant. The formulation or composition ingredients are selected to be consistent with the physical properties of copper(II) hydroxide and any other active ingredients, mode of application and environmental factors such as soil type, moisture and temperature. Useful formulations include liquids such as suspensions and the like which optionally can be thickened into gels. Useful formulations further include solids such as dusts, powders, granules, pellets, tablets, films (including seed coatings), and the like which can be water-dispersible ("wettable"). Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of copper(II) hydroxide and any other active ingredients, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Typical solid diluents are described in Watkins, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, glycerol esters, poly-oxyethylene/polyoxypropylene block copolymers, and alkylpolyglycosides where the number of glucose units, referred to as degree of polymerization (D.P.), can range from 1 to 3 and the alkyl units can range from $C_6$ to $C_{14}$ (see *Pure and Applied Chemistry* 72, 1255-1264). Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, propylene carbonate, dibasic esters, paraffins, alkylbenzenes, alkylnaphthalenes, glycerine, triacetine, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, acetates such as hexyl acetate, heptyl acetate and octyl acetate, and alcohols such as methanol, cyclohexanol, decanol, benzyl and tetrahydrofurfuryl alcohol.

Useful formulations of this invention may also contain materials well known to those skilled in the art as formulation aids such as antifoams, film formers and dyes. Antifoams can include water dispersible liquids comprising polyorganosiloxanes like Rhodorsil® 416. The film formers can include polyvinyl acetates, polyvinyl acetate copolymers, polyvinylpyrrolidone-vinyl acetate copolymer, polyvinyl alcohols, polyvinyl alcohol copolymers and waxes. Dyes can include water dispersible liquid colorant compositions like Pro-Ized® Colorant Red. One skilled in the art will appreciate that this is a non-exhaustive list of formulation aids. Suitable examples of formulation aids include those listed herein and those listed in *McCutcheon's 2001, Volume 2: Functional Materials* published by MC Publishing Company and PCT Publication WO 03/024222.

Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Stabilized copper(II) hydroxide refers to copper(II) hydroxide stabilized according to the present method.

Example A

High Strength Concentrate

| | |
|---|---|
| stabilized copper(II) hydroxide | 98.5% |
| silica aerogel | 0.5% |
| synthetic amorphous fine silica | 1.0%. |

Example B

Wettable Powder

| | |
|---|---|
| stabilized copper(II) hydroxide | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| stabilized copper(II) hydroxide | 10.0% |
| attapulgite granules (low volatile matter, 0.71/0.30 mm; U.S.S. No. 25-50 sieves) | 90.0%. |

Example D

Aqueous Suspension

| | |
|---|---|
| stabilized copper(II) hydroxide | 25.0% |
| hydrated attapulgite | 3.0% |
| crude calcium ligninsulfonate | 10.0% |
| sodium dihydrogen phosphate | 0.5% |
| water | 61.5%. |

Example E

Extruded Pellet

| | |
|---|---|
| stabilized copper(II) hydroxide | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

In fungicidal and bactericidal compositions the present stabilized copper(II) hydroxide can also be mixed with one or more other insecticides, fungicides, nematocides, bactericides, acaricides, growth regulators, chemosterilants, semiochemicals, repellents, attractants, pheromones, feeding stimulants or other biologically active compounds or agents to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, indoxacarb, isofenphos, malathion, metaldehyde, methamidophos, methidathion, methomyl, methoprene, methoxychlor, monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; fungicides such as acibenzolar, azoxystrobin, binomial, blasticidin-S, Bordeaux mixture (Tribasic copper sulfate), boscalid/nicobifen, bromuconazole, buthiobate, carpropamid (KTU 3616), captafol, captan, carbendazim, chloroneb, chlorothalonil, clotrimazole, copper oxychloride, copper salts, cyrmoxanil, cyproconazole, cyprodinil (CGA 219417),(S)-3,5-dichloro-N-(3-chloro-1-ethyl-1-methyl-2-oxopropyl)-4-methylbenzarnide (RH 7281), diclocymet (S-2900), diclomezine, dicloran, difenoconazole,(S)-3,5-dihydro-5-methyl-2-(methylthio)-5-phenyl-3-(phenylamino)-4H-imidazol-4-one (RP 407213), dimethomorph, dimoxystrobin (SSF-126), diniconazole, diniconazole-M, dodine, econazole, edifenphos, epoxiconazole (BAS 480F), famoxadone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, imazalil, 6-iodo-3-propyl-2-propyloxy-4(3H)-quinazolinone, ipconazole, iprobenfos, iprodione, isoconazole, isoprothiolane, kasugamycin, kresoxim-methyl, mancozeb, maneb, mefenoxam, mepronil, metalaxyl, metconazole, metominostrobin/fenominostrobin (SSF-126), miconazole, myclobutanil, neo-asozin (ferric methanearsonate), nuarimol, oxadixyl, penconazole, pencycuron, picoxystrobin, probenazole, prochloraz, propamocarb, propiconazole, pyraclostrobin, pyrifenox, pyrimethanil, prochloraz, pyrifenox, pyroquilon, quinoxyfen, spiroxamine, sulfur, tebuconazole, tetraconazole, thiabendazole, thifluzamide, thiophanate-methyl, thiram, triadimefon, triadimenol, triarimol, tricyclazole, trifloxystrobin, triforine, triticonazole, uniconazole, validamycin and vinclozolin; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi. The weight ratios of these various mixing partners to compounds of this invention typically are between 100:1 and 1:100, preferably between 30:1 and 1:30, more preferably between 10:1 and 1:10, and most preferably between 4:1 and 1:4.

In certain instances, combinations with other fungicides having a similar spectrum of control but a different mode of action will be particularly advantageous for resistance management.

Plant disease control is ordinarily accomplished by applying an effective amount of copper(II) hydroxide stabilized according to the present method (e.g., as a formulated composition) either pre- or post-infection, preferably pre-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

What is claimed is:

1. A method of stabilizing copper(II) hydroxide, the method comprising the sequential steps of:
   (a) combining copper(II) hydroxide, a water-soluble orthophosphate and water to form a mixture; and
   (b) drying the mixture.

2. The method of claim 1 wherein in (a) a dry copper(II) hydroxide powder is added to a combination of water and the water-soluble orthophosphate.

3. The method of claim 1 wherein in (a) a slurry of copper (II) hydroxide in water is added to a combination of water and the water-soluble orthophosphate.

4. The method of claim 1 wherein in (a) copper(II) hydroxide is added as a high moisture solid to a combination of water and the water-soluble orthophosphate.

5. The method of claim 1 wherein the copper(II) hydroxide is crystalline.

6. The method of claim 1 wherein the copper(II) hydroxide is prepared by oxidizing copper metal with oxygen in the presence of ammonia.

7. The method of claim 1 wherein the copper(II) hydroxide is prepared by a process using phosphate.

8. The method of claim 1 wherein the copper(II) hydroxide is prepared by a process using carbonate.

9. Stabilized copper(II) hydroxide prepared according to the method of claim 1.

10. A composition comprising stabilized copper(II) hydroxide prepared according to the method of claim 1 and at least one of a surfactant, a solid diluent or a liquid diluent.

* * * * *